United States Patent [19]
Lee et al.

[11] Patent Number: 5,338,540
[45] Date of Patent: Aug. 16, 1994

[54] HAIR WAVING AND STRAIGHTENING COMPOSITION

[75] Inventors: G. Jae Lee, Trumbull; Herbert Edelstein, Stratford, both of Conn.

[73] Assignee: Conopco, Inc., Greenwich, Conn.

[21] Appl. No.: 478,039

[22] Filed: Feb. 9, 1990

Related U.S. Application Data

[63] Continuation of Ser. No. 222,343, Jul. 20, 1988, abandoned, which is a continuation of Ser. No. 28,009, Mar. 18, 1987, abandoned, which is a continuation of Ser. No. 697,608, Feb. 4, 1985, abandoned.

[51] Int. Cl.$^5$ .............................................. A61K 7/09
[52] U.S. Cl. ...................................... 424/71; 424/72
[58] Field of Search ........................................... 424/71

[56] References Cited

U.S. PATENT DOCUMENTS

| | | | |
|---|---|---|---|
| 2,717,228 | 9/1955 | Brown | 424/71 |
| 2,836,185 | 5/1958 | Hervey | 424/71 |
| 3,912,808 | 10/1975 | Sokol | 424/71 |
| 3,954,960 | 5/1976 | Valan | 424/71 |
| 3,966,903 | 6/1976 | Torii et al. | 424/71 |
| 4,214,596 | 7/1980 | Kaplan | 424/71 |
| 4,243,659 | 1/1981 | Balingit et al. | 424/71 |
| 4,366,827 | 1/1983 | Madrange et al. | 424/71 |
| 4,445,521 | 5/1984 | Grollier et al. | 424/71 |

FOREIGN PATENT DOCUMENTS

| | | | |
|---|---|---|---|
| 921543 | 2/1960 | United Kingdom | 424/71 |

*Primary Examiner*—Dale R. Ore
*Attorney, Agent, or Firm*—Melvin H. Kurtz

[57] ABSTRACT

This invention relates to improved hair waving and straightening compositions of matter. The novel compositions of matter of this invention comprise a sulfite and/or bisulfite reducing system, urea, a cationic polyquaternary resin of such a nature that in combination with the urea in the reducing system a hair waving and/or straightening effect equivalent to conventional thioglycolate systems is effectuated without the attendant unpleasant odors associated with the thioglycolate systems. In addition, the reducing system of this invention is less damaging to the hair and skin than the thioglycolate systems. The system of course may be used either with or without heat such as heat from hair dryers. In order to achieve the above-mentioned objective, the compositions of this invention are at a pH in the range of above 5.5 to about 8.5, preferably 6.5. Such hair waving and straightening compositions may contain any conventional additives employed in the known sulfite and/or bisulfite (e.g. wetting agent, fragrance compounds, coloring agents, thickening agents, opacifying agents, sequestering agents, solubilizing agents, conditioning agents, etc.).

The novel hair waving and straightening compositions of this invention are used in conjunction with conventional neutralizing compositions used for conventional hair waving compositions. As is well-known, such neutralizing compositions contain oxidizing agents capable of restoring the disulfide linkages in the hair keratin during the resetting stage.

15 Claims, No Drawings

HAIR WAVING AND STRAIGHTENING COMPOSITION

This is a continuation of application Ser. No. 222,343 filed Jul. 20, 1988, now abandoned which is a continuation of co-pending application Ser. No. 07/028,009, filed on Mar. 18, 1987, and application Ser. No. 06/697,608, filed Feb. 4, 1985, (both now abandoned).

BACKGROUND OF THE INVENTION

It is well known that hair waving and straightening compositions containing thioglycolate as the reducing agent are very effective in the waving and straightening of hair. For example, when used in hair waving compositions, thioglycolate compounds give excellent curl/tightness characteristics to the hair. Such compositions have had substantial commercial acceptance. Illustrative of such compositions are those disclosed in U.S. Pat. No. 2,717,228 to Brown; U.S. Pat. No. 3,847,165 to Patel, et al; U.S. Pat. No. 2,631,965 to Schnell; U.S. Pat. No. 2,615,828 to Haefele; U.S. Pat. No. 2,836,185 to Hervey; and U.S. Pat. No. 3,071,515 to Wehr.

The thioglycolate hair waving and straightening compositions, however, have certain drawbacks associated therewith. First of all such compositions have a very unpleasant odor and, therefore, are troublesome to the consumer for use at home. Also, if used improperly on the hair or too often, such compositions present a possible risk of hair damage because of their effect on the physical properties of hair.

Another type of hair waving and straightening compositions which have had substantial commercial acceptance are those hair treating compositions containing sulfite and bisulfite salts (e.g. ammonium or alkali metal like sodium salts) as the reducing agent. For convenience sake, such compositions will be referred to herein as the sulfite/bisulfite systems.

While the sulfite/bisulfite systems do not have the unpleasant odor associated with the thioglyocolate systems, when used for waving hair, they do not impart to the hair the same "curl/tightness" imparted by the thioglycolate systems. Examples of known sulfite/bisulfite systems are those disclosed in U.S. Pat. No. 2,836,185 to Hervey; U.S. Pat. No. 3,864,476 to Altieri; U.S. Pat. No. 4,296,764 to Pallone et al; and U.S. Pat. No. 3,912,808 to Sokol, Belgian patent 895,854 and Belgian patent 892.348.

In the U.S. Sokol patent there is disclosed a hair straightening composition (Example 1) containing a bisulfite reducing system containing urea and a cationic quaternary polymer as a hair conditioner. In Sokol, the cationic resin is disclosed as a conditioning agent and not as an essential ingredient which will promote or enhance permanent waving or hair straightening.

OBJECT OF THE INVENTION

An object of this invention is to provide novel compositions of matter which will promote waving and straightening of the hair in an efficient manner similar to that obtained with thioglycolate systems but are free of the unpleasant odors associated with the thioglycolate systems as well as offering a lower risk of hair damage than is offered by thioglycolate systems.

Another object of this invention is to provide improved sulfite and/or bisulfite systems for the waving and straightening of hair.

A still further object of this invention is to provide improved sulfite and/or bisulfite hair waving compositions which give excellent hair curl characteristics.

GENERAL DESCRIPTION OF THE INVENTION

It has been found that the object of this invention may be realized by combining with a known sulfite and/or bisulfite reducing agent, urea, a known hydrogen bond breaker, in an amount of at least 12 percent by weight, and a cationic polyquaternary resin (or combinations thereof) having a conductivity, when measured at 0.1 percent by weight concentration, from $225^u$ mhos to $25^u$ mhos in an amount of at least 0.10 percent by weight, said composition having a pH in the range of 5.5 to 8.5.

The compositions of this invention perform in an unexpected manner when applied to hair. More particularly, the sulfite and/or bisulfite compositions of this invention containing urea and the cationic polyquaternaries together produce a level of curl tightness well above that possible with the urea or cationic polyquaternary by itself. In short, the combination of urea and polyquaternary effectuates an enhancement of curl tightness that is unexpected and well above what could reasonably be considered an additive result.

The compositions of the invention maybe used with or without the utilization of heat (e.g., heat from a hair dryer).

GENERAL FORMULA

1. Urea Component

In general, the urea is in an amount from about 10 percent to 20% by weight, preferably from 12 to 18% by weight. While amounts higher than 20% may be used no appreciable benefit appears to be obtained at such high amounts. When urea is in an amount somewhat higher than 18% such, for example, as 20 percent, there is no detrimental effect but there is also no gain in the amount of curl.

In providing the urea component in addition to urea itself derivatives of urea may be used such as those disclosed in the following patents:

U.S. Pat. No. 3,847,165—K. I. Patel which discloses urea, methyl urea, ethyl urea and mixtures thereof in a thiol waving system U.S. Pat. No. 3,339,682—T. Isdaji which discloses urea and thio urea in thioglycolic acid system U.S. Pat. No. 2,717,228—A. Brown which discloses urea and its alkyl derivatived in a thiol waving system U.S. Pat. No. 2,836,185—L. Hervey which discloses urea, urethane, formamide, and acetamide in a bisulfite waving system In applying the composition of the invention, the high concentration of urea and the cationic polyquaternary of the low conductivity mentioned earlier in combination with the sulfite and/or bisulfite, break the keratin bonds in such a manner that the composition gives excellent results as a hair waving and straightening composition. The urea component may be incorporated in the final composition just before use or added earlier if so desired.

2. Cationic Polyquaternary

As indicated earlier, the cationic polyquaternary has a conductivity, when measured at 0.1%, from $225^u$ mhos to $25^u$ mhos. The minimum concentration of cationic quaternary is about 0.07 percent by active weight basis and preferably at least 0.1%. Although the ease of hair combing increases as the cationic quaternary concentrate goes up e.g. 2.0 to 10%, the effect of the cationic quaternary concentration on curl/tightness levels off at around 0.5%. A particularly preferred concentration is from 0.4 to 1.0%.

Examples of suitable cationic polyquaternary are:
1. GAFQUAT 755N—quaternary copolymer of vinylpyrrolidone-dimethylaminoethyl methacrylate;
2. JR-125—Polymeric quaternary ammonium salt of hydroxyethyl cellulose trimethyl ammonium substituted epoxide;
3. CELQUAT L-200—A Hydroxyethyl cellulose—dimethyl diallyl ammonium chloride graft copolymer;
4. CELQUAT H-100—A Hydroxyethyl cellulose—dimethyl diallyl ammonium chloride graft copolymer;
5. BINAQAT P-100—Copolymer of acrylamide and methacryloyl oxyethylene trimethyl ammonium chloride.
6. POLYMAPTAC-Polymethyl acrylamidopropyl trimethyl ammonium chloride.

3. Wetting Agent

Any of the following groups of surface active agents can be used in addition to the polyquaternaries in the formula: cationic, non-ionic, compatible anionic, and amphoteric surface active agents. In general, the wetting agent is used in amounts conventionally used in hair waving such, for example, as up to 50% by weight and preferably 0.1 to 10.0 percent by weight.

4. Buffering Agent

Any or a combination of alkali metals, ammonium or amine phosphate, acetate, lactate salts, etc., which can help maintain the pH of the product within the specified pH range can be used. A preferred pH is in the range of 6.5 to 7.5 though the range can be between pH 5.5 to 8.5. At pH below 5.5 there is significant bisulfite breakdown resulting in a $SO_2$ odor generation.

5. Sulfite and/or Bisulfite Components

The sulfite and/or bisulfite component is in an amount conventionally used in hair waving and straightening compositions. In hair waving the broad range is 4 to 20% by weight and preferably 5 to 8%. For hair straightening the broad range is 4 to 20% by weight and preferably 8 to 12% by weight.

6. Other Ingredients

It is understood that fragrance compounds, coloring agents, thickening agents, opacifying agents, sequestrene agents, solubilizing agents, conditioning agents, etc. may be added to this invention in amounts conventionally used in hair waving and straightening compositions.

As indicated earlier, conventional neutralizer compositions may be used with the hair waving and straightening compositions of this invention.

The neutralizing chemicals used for our waving system are any of the oxidizing agents capable of restoring the disulfide linkages in the hair keratin during the resetting stage, such as aqueous solution of hydrogen peroxide, alkali metal bromates, alkali metal perborates, urea hydrogen peroxide, etc. while sodium sesquicarbonate may be used instead of the oxidizing agents for the new hair waving/straightening system. Rinsing alone with water may restore the broken linkages as well but it will be slower.

SPECIFIC DESCRIPTION OF THE INVENTION

The following Example I is a hair waving formulation produced in accordance with the present invention.

EXAMPLE 1

| Hair Waving Lotion | |
| --- | --- |
| Water, deionized | 73.89 |
| Polyoxyethylene (23) lauryl ether | 1.00 |
| Sequestrene (disodium EDTA) | 0.05 |
| Quaternary copolymer of vinyl pyrrolidone/ dimethylaminoethyl methacrylate | 0.60 |
| PEG-75 lanolin | 0.25 |
| Ammonium Bisulfite | 6.50 |
| Ammonium sulfite | 1.20 |
| Ammonia to pH 7.00 | 0.51 |
| Urea | 16.00 |
| | 100.00 |

EXAMPLE 2

| Part 1 | |
| --- | --- |
| Water, Deionized | 73.89 |
| Polyoxyethylene (23) lauryl ether | 1.00 |
| Sequestrene (disodium EDTA) | 0.05 |
| Quaternary copolymer of vinyl pyrrolidone/ dimethylaminoethyl methacrylate | 0.60 |
| PEG-75 lanolin | 0.25 |
| Ammonium Bisulfite | 6.50 |
| Ammonium sulfite | 1.20 |
| Ammonia (to pH 7) | 0.51 |
| | 84.00 |
| Part 2 | |
| urea | 16.00 |
| | 100.00 |

EXAMPLE 3

| | |
| --- | --- |
| Water, Deionized | 73.74 |
| Polyoxyethylene (23) lauryl ether | 1.00 |
| Sequestrene (disodium EDTA) | 0.05 |
| Hydroxyethyl cellulose-dimethyldiallyl ammonium chloride graft copolymer | 0.75 |
| PEG-75 lanolin | 0.25 |
| Ammonium Bisulfite | 6.50 |
| Ammonium sulfite | 1.20 |
| Ammonia (to pH 7) | 0.51 |
| Urea | 16.00 |
| | 100.00 |

EXAMPLE 4

| Part 1 | |
| --- | --- |
| Water, Deionized | 73.74 |
| Polyoxyethylene (23) lauryl ether | 1.00 |
| Sequestrene (disodium EDTA) | 0.05 |
| Hydroxyethyl cellulose-dimethyl diallyl ammonium chloride graft copolymer | 0.75 |
| PEG-75 lanolin | 0.25 |
| Ammonium Bisulfite | 6.50 |
| Ammonium sulfite | 1.20 |
| Ammonia (to pH 7) | 0.51 |
| | 84.00 |
| Part 2 | |

| | -continued | |
|---|---|---|
| Urea | | 16.00 |
| | | 100.00 |

In forming the above-mentioned formulation, Examples 1-4, the following procedure was employed.

METHOD OF PRODUCING THE EXAMPLES

1. Examples 1 and 3 (single package system) In a suitably sized container, weigh the right amount of water, polyoxyethylene (23) lauryl ether, sequestrene, polyquaternary, and PEG-75 lanolin. Heat to 120° F. with moderate agitation. Make sure all the solids are in solution. Then add urea with moderate agitation followed by ammonium bisulfite, ammonium sulfite, and ammonium hydroxide to pH of 7.0.

2. Examples 2 and 4 (two package system) These examples are prepared basically the same as for the examples 1 and 3 except no urea. In this system urea is packaged in a separate container and is mixed in the Part one container just prior to use.

A number of hair waving formulations were prepared and their ability to impart curl characteristics to hair was evaluated (Tables 1-4). The cationic polyquaternaries and quaternaries used in the abovementioned formulations are as follows:

1. GAFQUAT 755N—quaternary copolymer of vinyl pyrrolidone/dimethylaminoethyl methacrylate
2. POLYMER JR-125—Polymeric quaternary ammonium salt of hydroxyethyl cellulose trimethyl ammonium substituted epoxide
3. CELQUAT L-200—Hydroxyethyl cellulose—dimethyl diallyl ammonium chloride graft copolymer
4. CELQUAT H-100—Hydroxethyl cellulose—dimethyl diallyl ammonium chloride graft copolymer
5. CROQUAT-L—Lauryl dimethyl ammonium hydrolyzed collagen protein
6. BINAQAT P-100—Copolymer of acrylamide and methacryloyl oxyethylene trimethyl ammonium chloride
7. CARTARETIN F-4—Adipic acid—dimethylamino hydroxy propyl diethylene triamine copolymer
8. MIRAPOL A-15—Polyquaternary ammonium chloride (poly [N-3(dimethyl ammonio)propyl]N-[3—(ethylene oxyethylene dimethyl ammonio)-propyl]urea dichloride)
9. RETEN 210—Copolymer of acrylamide and beta metha acryloxyethyl trimethyl ammonium methosulfate
10. MERQUAT 100—Polymer of dimethyl diallyl ammonium chloride
11. MAQUAT SC-18-85—Stearalkonium chloride
12. SCHERCOQUAT 1AS—Isostearamide propyl ethyl dimonium ethosulfate
13. MERQUAT 550—Copolymer of dimethyl diallyl ammonium chloride and acrylamide
14. POLYMAPTIC—polymethyl acrylamidopropyl trimethyl ammonium chloride.

In the first group of formulations disclosed in Table I, a number of hair waving formulations (Examples A-Q) were prepared which had the same chemical makeup as the hair waving composition of Example 1 and Example 3 except that a different cationic material and/or a different amount of cationic material was used from that employed in Examples 1 and 3 with the amount of water being varied from that used in Examples 1 and 3 to make up for the difference between the amount of cationic material used in the example.

| Example | | |
|---|---|---|
| 1 | GAFQUAT 755N | 0.6% (by wt) |
| 3 | CELQUAT L-200 | 0.75% |
| A | CELQUAT L-200 | 1.00% |
| B | CELQUAT L-200 | 0.25% |
| C | GAFQUAT 755N | 1.00% |
| D | POLYMER JR-125 | 1.00% |
| E | MERQUAT 550 | 0.75% |
| F | BINAQUAT P-100 | 0.25% |
| G | POLYMAPTAC | 0.75% |
| H | MAQUAT SC-18 | 0.75% |
| J | SCHERCOQUAT 1AS | 0.75% |
| K | CROQUAT-L | 0.75% |
| L | CATARETIN F-4 | 0.75% |
| M | MIRAPOL A-15 | 0.75% |
| O | RETEN 21 | 0.75% |
| P | MERQUAT 100 | 0.75% |
| Q | None (no quaternary) | 0.00% |

When the above formulations were evaluated for hair waving performance, the results obtained for curl tightness are excellent for Example 1 thru G. In fact, the curl characteristics are similar to that obtained with typical thioglycolate system without the unpleasant odor. On the other hand, curl evaulations with formulations shown Example H through Q indicates that the curl tightness is much poorer than the thioglycolate system and Example 1 through G formulations.

In the second group of formulations (Examples R-X) shown in Table 2, the formulations of Example 3 was compared with the same base formula of Example 3 except urea is an amount of 0%, 5%, 10%, 12%, 14%, 18% and 20% instead of 16% along with an appropriate adjustment in the amount of water to make up the 100% by weight.

TABLE 2

| Example | |
|---|---|
| 3 | Urea 16% |
| R | Urea 20% |
| S | Urea 18% |
| T | Urea 14% |
| U | Urea 12% |
| V | Urea 10% |
| W | Urea 5% |
| X | Urea 0% |

When the above hair waving formulations were evaluated for curl tightness, Example 3 through V resulted in excellent curl characteristics similar to thioglycolate system, while the curl evaluations with Example W and X showed looser curls than the thioglycolate system and Example 3 through V formulations.

TEST COMPARING EXAMPLE 3 WITH A THIOGLYCOLATE COMPOSITION

OBJECTIVE: To evaluate and compare the above mentioned two permanent waving compositions.

PANEL PROFILE: 74 female panelists with various textures of virgin hair.

METHOD: Standard blind half-head comparison with two different versions of Neutralization.

VERSION 1-62 Panelists:

Example 3: Apply small amount of lotion to hair. Wind hair onto rollers. Reapply waving lotion, place plastic turban on head. Process 45 minutes. Rinse, towel blot. Neutralize 10 minutes, remove rods, rinse.

versus

THIOGLYCOLATE COMPOSITION ("TONI SILKWAVE"): Apply small amount of lotion to hair. Wind hair onto rollers. Reapply waving lotion. Process 15 minutes. No turban is used. Rinse, towel blot. Neutralize 5 minutes, remove rods, rinse.

CONCLUSION: Example 3 is significantly superior with no odor, very good curl tightness wet, good curl tightness dry, and no dry odor; whereas the thioglycolate composition has slight ammonia/thio odor wet, fair curl tightness wet, fair curl tightness dry, and slight odor dry. However, the thioglycolate composition has better dry combing (very good) compared to good dry combing for Example 3. There were no significant differences in the remaining categories. Both perms were equally good in wet combing, luster, soft feel, and manageability. They were equally very good with no static. There was no apparent damage to the hair.

VERSION 2–12 Panelists:

Example 3: Same procedure as in Version 1.

versus

THIOGLYCOLATE COMPOSITION: Apply small amount of lotion to hair. Wind hair onto rollers. Reapply waving lotion, process 15 minutes. No turban is used. Rinse, place dry towel over rolled curls and wait 30 minutes. Remove towel when time is up. Neutralize for 5 minutes, remove rods, and rinse.

CONCLUSION: Example 3 is significantly better with no odor wet or dry, and marginally better with good curl tightness on dry hair; whereas the thioglycolate composition has slight ammonia/thio odor wet and dry, and fair curl tightness on dry hair. Both perms were excellent in wet combing; very good in dry combing, luster, no static, and manageability; good in curl tightness wet and soft feel. There was no apparent damage to hair.

The following Examples 5–9 are hair straightening formulations produced in accordance with the present invention.

EXAMPLE 5

| | |
|---|---|
| Water, Deionized | 66.94 |
| Polyoxyethylene (23) lauryl ether | 1.00 |
| Hydroxyethyl cellulose dimethyl diallyl ammonium chloride graft copolymer | 0.75 |
| PEG-75 lanolin | 0.25 |
| Hydroxyethyl cellulose | 1.50 |
| Urea | 18.00 |
| Ammonium Bisulfite | 9.00 |
| Ammonium Sulfite | 2.00 |
| Ammonia to pH - 7.0 | 0.56 |
| | 100.00 |

EXAMPLE 6

| | |
|---|---|
| Part 1 | |
| Water, Deionized | 68.44 |
| Polyoxyethylene (23) lauryl ether | 1.00 |
| Hydroxyethyl cellulose dimethyl diallyl ammonium chloride graft copolymer | 0.75 |
| PEG-75 lanolin | 0.25 |
| Ammonium Bisulfite | 9.00 |
| Ammonium Sulfite | 2.00 |
| Ammonia to pH - 7.0 | 0.56 |
| | 82.00 |
| Part 2 | |
| Urea | 18.00 |
| | 100.00 |

EXAMPLE 7

| | |
|---|---|
| Water, Deionized | 66.69 |
| Polyoxyethylene (23) lauryl ether | 1.00 |
| Quaternary copolymer of vinyl pyrrolidone/dimethylaminoethyl methacrylate | 1.00 |
| PEG-75 lanolin | 0.25 |
| Hydroxyethyl cellulose | 1.50 |
| Urea | 18.00 |
| Ammonium Bisulfite | 9.00 |
| Ammonium Sulfite | 2.00 |
| Ammonia to pH - 7.0 | 0.56 |
| | 100.00 |

EXAMPLE 8

| | |
|---|---|
| Part 1: | |
| Water, Deionized | 68.19 |
| Polyoxyethylene (23) lauryl ether | 1.00 |
| Quaternary copolymer of vinyl pyrrolidone/dimethylaminoethyl methacrylate | 1.00 |
| PEG-75 lanolin | 0.25 |
| Ammonium Bisulfite | 9.00 |
| Ammonium Sulfite | 2.00 |
| Ammonia to pH - 7.2 | 0.56 |
| | 82.00 |
| Part 2 | |
| Urea | 18.00 |
| | 100.00 |

EXAMPLE 9

| | |
|---|---|
| Water, Deionized | 66.44 |
| Polyoxyethylene (23) lauryl ether | 1.00 |
| Quaternary copolymer of vinyl Pyrrolidone/dimethylaminoethyl methacrylate | 1.00 |
| Polymeric quaternary ammonium salt of Hydroxyethyl cellulose trimethyl ammonium substituted epoxide | 0.25 |
| Hydroxyethyl cellulose | 1.50 |
| PEG-75 lanolin | 0.25 |
| Urea | 18.00 |
| Ammonium bisulfite | 9.00 |
| Ammonium sulfite | 2.00 |
| Ammonium to pH - 7.0 | 0.56 |
| | 100.00 |

As indicated earlier, the compositions of this invention not only perform in an manner comparable to thioglycolates a hair waving and straightening formulation without the undesirable malodors associated with thioglycolates but they also are a lesser risk than alkaline thioglycolates for causing hair damage if misused by the consumer.

That compositions of the present invention are less of a risk than thioglycolates with respect to hair damage is shown by the now-described experiments to determine the effects of multiple perms on the physical properties of hair, i.e. are the hair waving compositions evaluated drying and damaging to the hair and, if so, how much.

SYSTEM A (Bisulfite/Sulfite/Polyquaternary)

This system A uses a bisulfite/sulfite/polyquat hair waving formulation and a neutralizer which are of the following formulae:

| | % by weight |
|---|---|
| System A Hair Waving Lotion - Bisulfite/Polyquat System | |
| Laureth-23 | 1.00 |
| Sequestrene (disodium EDTA) | 0.05 |
| Hydroxytehyl cellulose-dimethyl diallyl ammonium chloride - graft copolymer | 0.75 |
| Ammonium Bisulfite | 6.50 |
| Ammonium Sulfite | 1.20 |
| Monoethanolamine (to pH - 7.0) | 1.90 |
| Water, Deionized q.s. to | 100.00% |
| System A - Neutralizer | |
| Hydrogen Peroxide 35% | 3.7142 |
| Phosphoric Acid (85%) (to pH - 2.5) | 0.08 |
| Acetophenetidin | 0.012 |
| Water, High Resistance to | 100.00% |

SYSTEM B (Urea/Bisulfite/Sulfite/Polyquaternary)

This system employs the hair waving composition of Example 3 and the same neutralizer described above with System A.

| System B Hair Waving Lotion - Bisulfite/Sulfite/Urea/Polyquat | |
|---|---|
| | % by weight |
| Laureth 23 | 1.00 |
| Sequestrene (disodium EDTA) | 0.05 |
| Hydroxyethyl cellulose-dimethyldiallyl-ammonium chloride graft copolymer | 0.75 |
| PEG-75 lanolin | 0.25 |
| Ammonium Bisulfite | 6.50 |
| Ammonium Sulfite | 1.20 |
| Urea | 16.00 |
| Ammonia (to pH - 7.0) | 0.51 |
| Water, Deionized q.s. to | 100.00% |

SYSTEM C (An Alkaline Thioglycolate) This system may be exemplified by the commercial alkaline thioglycolate system sold under the trade name "TONI SILKWAVE".

The evaluation was done on virgin brown hair, using an "exploratory" sample size of ten fibers. Each perm was evaluated after one, two and three treatments.

METHOD AND RESULTS

Method

The Biophysical evaluation was done on virgin brown hair. The sample size was ten fibers/test. Each perm was evaluated after one, two and three treatments. Individual fibers were cut in half to provide an untreated control half and a treated half, which was wound onto a ¼" nylon permanent wave rod. The perm processing times were 60 minutes for the bisulfite/sulfite/polyquaternary, 45 minutes for the urea/bisulfite/sulfite/polyquaternary, and 20 minutes for the alkaline thioglycolate system. Before treating, all fibers were equilibrated at least 24 hours at 21° C. and 20% relative humidity. Between each perm the fibers were shampooed four times. The Instron tensile tester was used to produce stress strain curves on the fibers.

Results

It was obvious that the perming systems are drying and damaging to the hair, especially after three perms. However, there are differences between them. The differences in each category are significant from perm to perm. That is, the alkaline thio system is significantly more drying and more damaging than the urea/bisulfite/sulfite/polyquaternary perm whether after one, two, or three perms. Likewise, the urea/bisulfite/sulfite/polyquaternary perm is more damaging than the bisulfite/sulfite/polyquaternary perm.

What is claimed is:

1. In a hair waving or straightening composition of matter consisting essentially of a sulfite and/or bisulfite system having pH in the range of 5.5 to 8.5, the improvement which comprises: including in said reducing system the combination of urea in an amount of 10 to 20% by weight and at least 0.07% by weight of at least one cationic polyquaternary compound having a conductivity, when measured at 0.1% by weight concentration, from 225 micro mhos to 25 micro mhos.

2. In a hair waving or straightening composition according to claim 1 wherein the cationic polyquaternary is selected from the group consisting of quaternary copolymers of vinyl pyrrolidone/dimethylaminoethyl methacrylate, polymeric quaternary ammonium salt of hydroxyethyl cellulose trimethyl ammonium substituted epoxide, hydroxyethyl cellulose-dimethyl diallyl ammonium chloride graft copolymer, copolymer of acrylamide and methylacryloyl oxyethylene trimethyl ammonium chloride, and polymethyl acrylamidopropyl trimethyl ammonium chloride and combinations of the foregoing.

3. In a hair waving or straightening composition according to claim 1 or 2 wherein there is included a wetting agent in addition to the polyquaternary component.

4. A hair waving or straightening composition according to claim 1 or 2 wherein there is included in addition to the polyquaternary component a wetting agent selected from the group consisting of cationic, non-ionic, compatible anionic and amphoteric surface active agents.

5. In a hair waving or straightening composition according to claims 1 or 2 wherein the composition has a pH in the range of 6.5 to 7.5.

6. In a hair waving or straightening composition according to claim 1 or 2 wherein there is included a buffering agent.

7. In a hair waving or straightening composition according to claim 1 or 2 wherein there is included a buffering agent selected from the group consisting of alkali metals, ammonium and amino phosphate, acetate and lactate salts.

8. In a hair waving or straightening composition according to claim 1 or 2 wherein the reducing agent comprises a bisulfite salt.

9. In a hair waving or straightening composition according to claim 1 or 2 wherein the reducing agent comprises a sulfite salt.

10. In a hair waving or straightening composition according to claim 1 or 2 wherein the reducing agent comprises a sulfite/bisulfite mixture.

11. In a hair waving or straightening composition according to claim 1 or 2 wherein the cationic polyquaternary is hydroxyethyl cellulose-dimethyl diallyl ammonium chloride graft copolymer.

12. In a hair waving or straightening composition according to claim 1 or 2 wherein the cationic polyquaternary is a quaternary copolymer of vinyl pyrrolidone/dimethylaminoethyl methacrylate.

13. In a hair waving composition according to claim 1 having the formula:

| | |
|---|---|
| Water, deionized | 73.89 |
| Polyoxyethylene (23) lauryl ether | 1.00 |
| Sequestrene (disodium EDTA) | 0.05 |
| Quaternary copolymer of vinyl pyrrolidone/ | 0.60 |
| dimethylaminoethyl methacrylate | 0.60 |
| PEG-75 lanolin | 0.25 |
| Ammonium Bisulfite | 6.50 |
| Ammonium Sulfite | 1.20 |
| Ammonia (to pH 7.0) | 0.51 |
| Urea | 16.00 |
| | 100.00 |

14. In a hair straightening composition according to claim 1 having the formula:

| | |
|---|---|
| Water, Deionized | 66.44 |
| Polyoxyethylene (23) lauryl ether | 1.00 |
| Quaternary copolymer of vinyl pyrrolidone/dimethylaminoethyl methacrylate | 1.00 |
| Polymetic quaternary ammonium salt of hydroxyethyl cellulosse trimethyl ammonium substituted epoxide | 0.25 |
| Hydroxyethyl cellulose | 1.50 |
| PEG-75 lanolin | 0.25 |
| Urea | 18.00 |
| Ammonium Bisulfite | 9.00 |
| Ammonium Sulfite | 2.00 |
| Ammonia (to pH - 7.0) | 0.56 |
| | 100.00 |

15. The method of waving or straightening hair comprising applying to the hair to be waved or straightened the composition of claim 1.

* * * * *